United States Patent [19]

Duffett et al.

[11] Patent Number: Plant 5,776

[45] Date of Patent: Aug. 5, 1986

[54] CARNATION PLANT NAMED WINSOME

[75] Inventors: William E. Duffett, Salinas; Walter H. Jessel, Jr., Fremont, both of Calif.

[73] Assignee: Yoder Brothers, Inc., Barberton, Ohio

[21] Appl. No.: 671,889

[22] Filed: Nov. 15, 1984

[51] Int. Cl.[4] ..... A01H 5/00

[52] U.S. Cl. ..... Plt./71

[58] Field of Search ..... Plt./71

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar named Winsome, particularly described as to uniqueness by the combined characteristics of miniature or spray type, commerical double form, 6.0 to 8.0 cm. flower diameter, lavender (red-purple) color, 16 to 18 weeks for response, 10 to 12 flowers and buds per stem, 5 to 8 cm. peduncle length, rigid peduncle strength, 86 to 90 cm. plant height, and strong, spice fragrance.

2 Drawing Figures

The present invention comprises a new and distinct cultivar of *Dianthus caryophyllus, Linn.* named Winsome.

Winsome is the product of a planned breeding program which had the objective of creating new spray type carnation cultivars in a wide color range with fast flowering response, unrestricted breaking action, vigorous growth, strong, non-brittle stems, high bud and flower count and attractive, durable flowers for year round commercial production.

Winsome was originated from a hybridization made in Barberton, Ohio in the year 1973 between 64019024, an unnamed seedling as female, and 71179002, an unnamed seedling as male.

Winsome was discovered and selected as one flowering plant within a progeny of the stated parentage by William E. Duffett and Walter H. Jessel, Jr. in August 1974 in a controlled environment in Barberton, Ohio.

The first act of asexual reproduction of Winsome was accomplished when vegetative cuttings were taken from the initial selection on November 1974 in a controlled environment in Barterton, Ohio by a technician under formulations established and supervised by William E. Duffett and Walter H. Jessel, Jr.

Horticultural examination of selected units initiated in 1975 has demonstrated that the combination of characteristics as herein disclosed for Winsome are firmly fixed and are retained through successive generations of asexual reproduction.

Winsome has not been observed under all possible environmental conditions. The phenotype may vary significantly with variations in the environment such as temperature, light intensity and day length. The following observations, measurements and comparisons describe plants grown in Salinas, Calif. under greenhouse conditions which approximate those generally used in commercial practice.

The following traits have been repeatedly observed and are determined to be basic characteristics of Winsome which in combination distinguish this carnation as a new and distinct cultivar:

1. Miniature type or spray carnation.
2. Commercial double form; average number of petals is 78.
3. Petal length is 5.0 cm.; width is 3 cm.; diameter at maturity is 6.0 to 8.0 cm.

4. Lavender (red-purple) color.
5. Average response is 16 to 18 weeks including time from plant to pinch, and pinch to peak harvest.
6. Average bud count is 10 to 12.
7. Peduncle length is 5 to 8 cm.
8. Vigor is strong, prolific. Height at first harvest is 86 to 90 cm.
9. Stem length is 65 to 70 cm.; strong.
10. Strong spice fragrance.

Among the commercially available carnations known to the present inventors, the most similar in comparison to Winsome is Improved Lilac, a commercially available variety. Reference is made to Chart A which compares certain characteristics of Improved Lilac with those same characteristics of Winsome. General comparisons are as follows. Winsome has deeper color, larger flower diameter, higher bud count, shorter peduncle length, taller plant height, and a serrated edge as contrasted to the even petal edge of Improved Lilac. Both cultivars have similar response time and strong, rigid stems.

In the accompanying photographic drawings Sheet 1 is a color photograph showing typical infloresence and foliage characteristics of Winsome, with color as nearly true as possible with illustrations of this type. Sheet 2 is a black and white photograph showing three views of the inflorescence of Winsome.

In the following description color references are made to The Royal Horticultural Society Colour Chart. Color values were determined between 10:00 A.M. and 10:15 A.M. on Apr. 3, 1984 under 380 foot-candle light at Salinas, Calif.

Classification:

*Botanical.*—*Dianthus caryophyllus, Linn.* cv WINSOME.

*Commercial.*—Spray carnation for cut flower production.

I. Inflorescence characteristics:

*Flowering response.*—16 to 18 weeks.

*Inflorescence type.*—Miniature or spray with center buds removed.

*Number of buds and flowers per stem.*—10 to 12.

*Peduncle length.*—5 to 8 cm.

*Peduncle strength.*—Rigid, strong.

*Flower.*—Form: Commercial double. Size: 6.0 to 8.0 cm. diameter. Petal edge: Serrated. Petal count: 78. Petal size: Average length 5.0 cm.; average width 3 cm. Bud shape: Ovoid. Pointed tip. Splitting tendency: Minimal. Slab tendency: None. Keeping Quality: Vase life from stage IV is 8 days. Fragrance: Strong, spice fragrance.

*Reproduction organs.*—Androecium: 8 or more filaments; 8 or more anthers; abundant pollen. Gynoecium: 2 styles; 2 stigmas; 1.5 cm. length.

*Corolla color.*—General tonality from a distance of three meters: Lavender (red-purple). Upper surface: 73 B,C, with specks of 73A. Base: 154D. Under surface: 68D. Base: 154D. Color stability: Uniform. Seasonal variations: Minimal. Calyx: Size: 3.0×1.5 cm. at maturity. Shape: Urn shaped. Number of sepals: Normally five (5), at times six (6).

*Plant characteristics.*—Growth and duration: Vigorous and continuous at 12° C. minimum temperature. Branching pattern: Vegetative laterals at 7th and 8th nodes. Height: Single pinched plant, first cut — 86 to 90 cm. Stem: Length — 65 to 70 cm. Bending traits — Normally rigid with 10 to 15 degrees of bend.

*Foliage.*—Occurrence: Shape — Long, narrow; length 18 to 20 cm. Texture: Smooth. Displacement: Opposite at nodes.

*Color.*—Mature: Upper surface — 137A, B. Mature: Under surface — 139B. Immature: Upper surface — 138A. Immature: Under surface — 138A.

CHART A

COMPARISON OF WINSOME AND IMPROVED LILAC

| FLOWER | AVERAGE FLOWER |
|---|---|

CHART A-continued

COMPARISON OF WINSOME AND IMPROVED LILAC

| CULTIVAR | COLOR | SIZE |
|---|---|---|
| WINSOME | LAVENDER RED-PURPLE | DIAMETER OF 6.0 to 8.0 cm. SERRATED PETAL EDGE |
| IMPROVED LILAC | LIGHT LAVENDER | DIAMETER OF 5.5 to 6.0 cm. SMOOTH PETAL EDGE |

| CULTIVAR | AVERAGE BUDS & FLS. PER STEM | AVERAGE FLOWERING RESPONSE |
|---|---|---|
| WINSOME | 10 to 12 5 WITH COLOR | 16 to 18 WEEKS |
| IMPROVED LILAC | 6 to 7 4 WITH COLOR | 16 to 18 WEEKS |

| CULTIVAR | AVERAGE PEDUNCLE LENGTH | AVERAGE PEDUNCLE STRENGTH | AVERAGE PLANT HEIGHT |
|---|---|---|---|
| WINSOME | 5 to 8 cm. | RIGID | 86 to 90 cm. |
| IMPROVED LILAC | 5 to 16 cm. | RIGID | 60 to 70 cm. |

COMPARISONS MADE OF PINCHED, FLOWERING PLANTS GROWN AS SPRAYS WITH CENTER BUDS REMOVED IN SALINAS, CALIFORNIA

We claim:

1. A new and distinct cultivar of *Dianthus caryophyllus, Linn.*, named Winsome, as described and illustrated, and particularly characterized as to uniqueness by the combined characteristics of miniature or spray type, commercial double form, 6.0 to 8.0 cm. flower diameter, lavender (red-purple) color, 16 to 18 weeks for response, 10 to 12 flowers and buds per stem, 5 to 8 cm. peduncle length, rigid peduncle strength, 86 to 90 cm. plant height, and strong, spice fragrance.

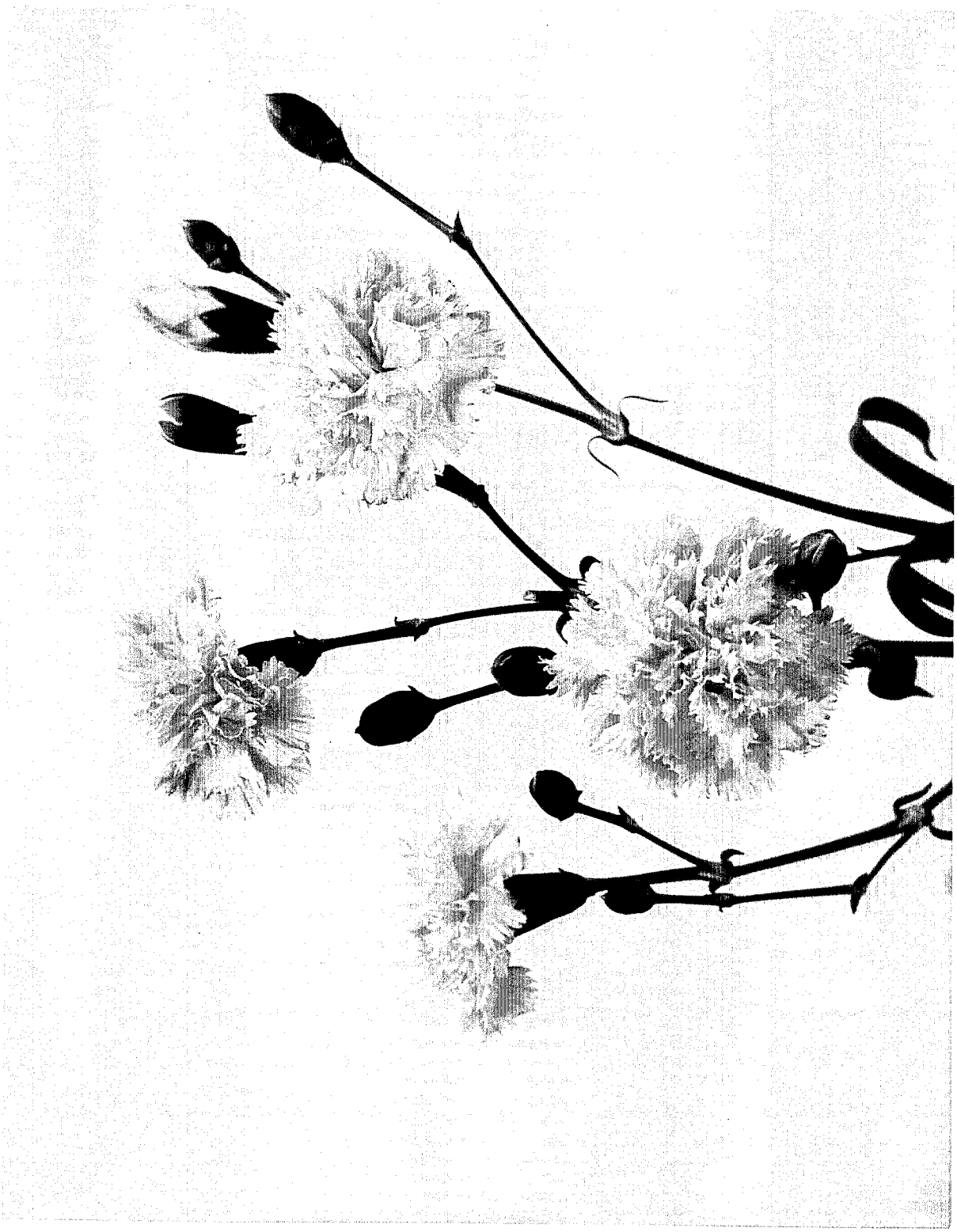

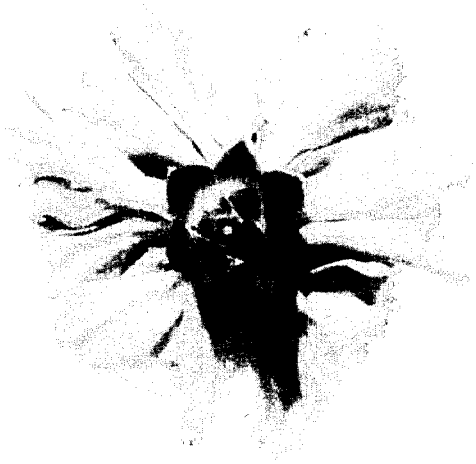
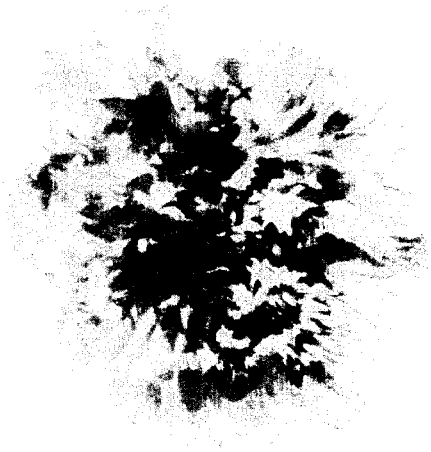
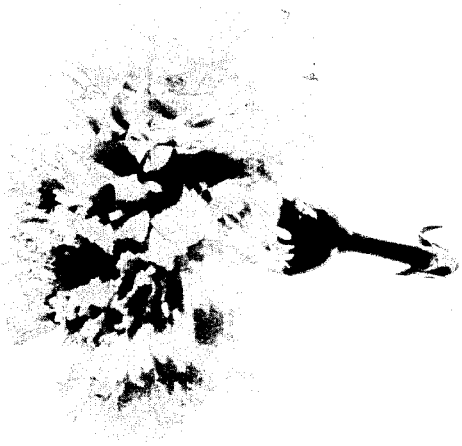

* * * * *